United States Patent [19]

Bevilacqua et al.

[11] Patent Number: 5,527,785

[45] Date of Patent: Jun. 18, 1996

[54] SELECTIN RECEPTOR MODULATING COMPOSITIONS

[75] Inventors: Michael P. Bevilacqua; Richard M. Nelson, both of San Diego, Calif.; Robert J. Linhardt, Iowa City, Iowa

[73] Assignee: The Regents of the University of California, Oakland, Calif.

[21] Appl. No.: 89,076

[22] Filed: Jul. 7, 1993

Related U.S. Application Data

[63] Continuation-in-part of Ser. No. 62,957, May 14, 1993, abandoned.

[51] Int. Cl.[6] .......................... A61K 31/725; C08B 37/10
[52] U.S. Cl. .................. 514/56; 514/54; 514/61; 536/21
[58] Field of Search ............................ 514/56, 54, 61; 536/21

[56] References Cited

U.S. PATENT DOCUMENTS

| | | | |
|---|---|---|---|
| 5,143,712 | 9/1992 | Brandley et al. | 424/1.73 |
| 5,208,253 | 5/1993 | Boschelli et al. | 514/443 |
| 5,211,937 | 5/1993 | Brandley et al. | 424/1.73 |
| 5,227,369 | 7/1993 | Rosen et al. | 514/23 |
| 5,268,364 | 12/1993 | Kojima et al. | 514/25 |

OTHER PUBLICATIONS

R. M. Nelson et al. *J. Clin. Invest.*, Mar. 1993, vol. 91, 1157–1116.
M. P. Bevilacqua et al. *J. Clin. Invest.*, Feb. 1993, vol. 91, 379–387.
Assays for inhibitors of leukocyte adhesion Steven, et al., *Chemical Abstracts*, No. 9, 118:390, Mar. 1, 1993.
GMP–140 (P–selectin/CD62) binds to chronically stimulated but not resting CD4+T lymphocytes and regulates their production of proinflammatory cytokines Damle, et al., *Eur. J. Immunol.*, 22:1789–1793, 1992.
Selectins Bevilacqua & Nelson, *Perspectives*, 91:379–387, Feb. 1993.
Characterization of Human Platelet GMP–140 as a Heparin–Binding Protein Skinner, et al., *Biochemical & Biophysical Research Comm.*, No. 3, 164:1373–1379, Nov. 15, 1989.
GMP–140 Binding to Neutrophils Is Inhibited by Sulfated Glycans Skinner, et al., *The Jrnl. of Biological Chemistry*, No. 9, 266: 5371–5374, Mar. 25, 1991.
Degradation of Glycosaminoglycans and Fibronectin on Endotoxin–Stimulated Endothelium by Adherent Neutrophils: Relationship to CD11b/CH18 and L–Selectin . . . Klein, et al., *The Jrnl. of Infect. Diseases*, No. 4, 167:890–898, Apr. 1993.
Calcium–Dependent Heparin–Like ligands for L–Selectin in Nonlymphoid Endothelial Cells Norgard–Sumnicht, et al., *Science*, 261:480–483, Jul. 23, 1993.
Heparin Oligosaccharides bind L– and P–Selectin and Inhibit Acute Inflammation Nelson, et al., *Blood*, No. 11, 82:3253–3258, Dec. 1, 1993.

*Primary Examiner*—Douglas W. Robinson
*Assistant Examiner*—Kathleen Kahler Fonda
*Attorney, Agent, or Firm*—Fish & Richardson

[57] ABSTRACT

Selectin receptor binding is modulated by a method which utilizes heparin-like oligosaccharides.

7 Claims, 11 Drawing Sheets

ΔUA2S(1-4)-α-GlcNS6S(1-4)-α-IdoA2S-(1-4)-α-GlcNS6S

SELECTIN RECEPTOR MODULATING COMPOSITIONS

This application is a continuation-in-part of application Ser. No. 08/062,957, filed May 14, 1993, now abandoned.

BACKGROUND OF THE INVENTION

1. Field of the Invention

The present invention relates generally to the field of cell adhesion molecules and specifically to the use of oligosaccharide compositions for modulating selectin receptor binding.

2. Description of Related Art

Cell adhesion molecules (CAMs) play a role in inflammation, infection, cancer and other disease processes. Recent advances in cloning and protein sequencing have led to the organization of CAMs into families, based on their molecular structure. Intense research has been focused on selectins, which are carbohydrate-binding proteins expressed on endothelial and leukocyte surfaces; B2 integrins, which are heterodimeric proteins found on the surfaces of leukocytes; and proteins of the immunoglobulin type such as intracellular adhesion molecule, ICAM-1 and ICAM-2 which occur on many different cell surfaces.

The mechanism of inflammation can be understood in terms of CAM interactions. Leukocyte adhesion to the vessel wall is a key step in the development of inflammatory and immunological processes. Adhesion molecules that support these interactions include the selectins, a group of CAMs which are named for the cell type on which they were originally identified. The selectins include E-selectin (endothelial cells), P-selectin (platelets and endothelial cells) and L-selectin (lymphocytes).

The three selectins act in concert with other cell adhesion molecules (e.g., ICAM-1, vascular cell adhesion molecule-1 and the leukocyte integrins) to effect adhesive interactions of leukocytes, platelets and endothelial cells. E-selectin was first shown to support the adhesion of neutrophils to cytokine-activated endothelium (Bevilacqua, et al., *Proc. Natl. Acad. Sci.*, USA. 84:9238, 1987; Bevilacqua, et al., *Science* 243:1160, 1989). Subsequent studies in vitro have suggested that E-selectin also supports the binding of monocytes, a sub-population of memory T lymphocytes, eosinophils and basophils. Similarly, P-selectin also supports leukocyte adhesion. In addition to its role in lymphocyte homing, L-selectin appears to participate in the adhesion of neutrophils, monocytes and lymphocytes to activated endothelium (reviewed in Bevilacqua, M. and Nelson, R., *J. Clin. Invest.* 91:379, 1993).

Selectins contain domains homologous to C-type lectins, therefore there has been an intensive search for carbohydrate ligands. Many recent studies on selectin-carbohydrate interactions have focused on oligosaccharides. P- selectin-dependent rosetting of activated platelets to leukocytes is blocked by LNF-III, a pentasaccharide containing the Lewis x determinant (Le$^x$; Galβ1– 4(Fucα1–3)GlcNAc) (Larsen, et al., *Cell*, 63:467, 1990). Other studies identified the sylated form of this oligosaccharide, sLe$^x$ (Neu5Acα2–3Galβ1–4(Fucα1–3)GlcNAc) and/or closely related structures as ligands of E-selectin. sLe$^x$ and other fucosylated lactosamines are found in abundance on circulating neutrophils and monocytes and on a small percentage of blood lymphocytes (reviewed in Bevilacqua, M. and Nelson, R., supra). Separate studies have demonstrated that sialic acid is a component of some P-selectin ligands, and that oligosaccharides containing sLe$^x$ are recognized by this molecule. In addition, human E- and P-selectin and murine L-selectin have been shown to interact with molecules containing sLe$^a$ (Neu5Acα2–3Galβ1–3(Fucα1–4)GlcNAc), a structural isomer of sLe$^x$. sLe$^a$ is not typically expressed by blood leukocytes, but is expressed by certain cancer cells, suggesting a possible role in metastasis.

In response to certain mediators like thrombin and histamine, endothelial cells redistribute P-selectin from storage granules to the surface within minutes. In response to endotoxin, IL-1, or TNF, endothelial cells biosynthesize and express E-selectin as well as VCAM-1 and ICAM-1 over a period of hours to days. L-selectin is constitutively expressed by leukocytes and appears to recognize a cytokine-induced endothelial cell surface ligand. Inflammatory processes are essential for host defense against pathogens. When control mechanisms fail or the pathogen burden is too great, the inflammation becomes extreme. The ensuing tissue damage contributes to important human diseases such as rheumatoid arthritis, ischemic reperfusion injury, autoimmune diseases, and adult respiratory distress syndrome (ARDS).

Heparins are widely used therapeutically to prevent and treat venous thrombosis. Apart from interactions with plasma components such as antithrombin III or heparin cofactor II, interactions with blood and vascular wall cells may underlie their therapeutic action. The term heparin encompasses to a family of unbranched polysaccharide species consisting of alternating 1→4 linked residues of uronic acid (L-iduronic or D-glucuronic) and D-glucosamine. Crude heparin fractions commonly prepared from bovine and porcine sources are heterogeneous in size (5,000–40,000 daltons), monosaccharide sequence, sulfate position, and anticoagulant activity. Mammalian heparin is synthesized by connective tissue mast cells and stored in granules that can be released to the extracellular space following activation of these cells. Overall, heparin is less abundant than related sulfated polysaccharides, such as heparan sulfate, dermatan sulfate, and chondroitin sulfate, which are synthesized in nearly all tissues of vertebrates. Heparin and these other structures are commonly referred to as glycosaminoglycans.

The anticoagulant activity of heparin derives primarily from a specific pentasaccharide sequence present in about one third of commercial heparin chains purified from porcine intestinal mucosa. This pentasaccharide, —αGlcNR$_1$6Sβ(1–4)GlcAα(1–4)GlcNS3S6R$_2$α(1–4)IdoA2Sα(1–4)GlcNS6S where R$_1$=—SO$_3^-$ or —COCH$_3$ and R$_2$=—H or —SO$_3^-$, is a high affinity ligand for the circulating plasma protein, antithrombin (antithrombin III, AT-Ill), and upon binding induces a conformational change that results in significant enhancement of antithrombin's ability to bind and inactivate coagulation factors, thrombin, Xa, IXa, VIIa, XIa and XIIa. For heparin to promote antithrombin's activity against thrombin, it must contain the specifically recognized pentasaccharide and be at least 18 saccharide units in length. This additional length is believed to be necessary in order to bridge antithrombin and thrombin, thereby optimizing their interaction.

Much of the recent work on selectin-carbohydrate interactions has focused on oligosaccharides based on Le$^x$, Le$^a$, and sialylated and sulfated derivatives of these structures. While crude fractions of heparin have been reported to bind and inhibit P-selectin-dependent and L-selectin-dependent interactions, no reports have shown studies on binding of small heparin fragments to the selectins. The specificity of heparin binding to the selectins is unclear, although other sulfated polysaccharides such as fucoidan and dextran sulfate also bind to P-selectin and L-selectin.

Crude heparin fractions have been reported to affect the activity of mast cell granule components, including histamine, and have been known to dampen allergic responses (Higginbotham, et al., P.S.E.B.M. 92:493, 1956; Carr, J., Thromb. Res 16:507, 1979). In rat models, heparin causes enhancement of certain platelet responses (Srivastava, et al., Biochem. Pharmacol. 40:357, 1990), reduction of carrageenin-induced footpad edema (Hanahoe, et al., Int. Arch. Allergy Appl. Immunol., 86:243, 1988), and inhibition of allergic encephalomyelitis (Willenborg, et al., J. Immunol. 140:3401, 1988). Inhaled heparin in a sheep model reduced antigen-induced bronchoconstriction (Ahmed, et al., Am. Rev. Respir. Dis., 145:566, 1992). Crude (unfractionated) heparins have also been observed to modulate various immune responses in animal models (Gorski, et al., FASEB J. 5:2287, 1991). These include delayed-type hypersensitivity reactions (DTH), allograft rejection, and immune cell-mediated killing. Tumor metastasis may also be affected by heparin. Most of these studies described above used crude heparin fractions of average molecular weight approximately 12000–15000 (40–50 saccharide residues) which would also possess significant anticoagulant activity.

Thus, considerable need exists for compositions with the biocompatibility and antiinflammatory properties of crude heparin without the danger of systemic anticoagulant activity. The present invention provides such compositions.

SUMMARY OF THE INVENTION

The present invention provides a method of modulating selectin receptor binding in a subject comprising administering to the subject an effective amount of an oligosaccharide which binds to the selectin receptor, wherein the oligosaccharide has the structure of a heparin-like molecule containing from about 2 to about 50 saccharide units. Oligosaccharides greater than 18 saccharide units are antithrombin-binding-pentasaccharide free. Preferably, the oligosaccharide binds to the P- and L-selectin receptor.

Small fragments with this structure have little or no activity in antithrombin-dependent inactivation of thrombin and little or no activity in antithrombin-dependent inactivation of factor Xa or other coagulation factors. These smaller molecules can also be used in higher concentrations in vivo without risk of bleeding, and without other complications associated with higher molecular weight forms of heparin. The function of selectins suggests their involvement in a wide variety of human diseases associated with inflammation. These range from acute appendicitis to asthma, myocardial infarction, specific immunological disease processes, infection with viruses or bacteria, malignancy and metastasis, and reperfusion injury. Antiinflammatory compounds which contain heparin-like sequences, which block selectin-dependent adhesion directly, would be useful in modulating the selectin-dependent adhesion associated disorders in a subject.

DETAILED DESCRIPTION OF THE INVENTION

Figure 1:
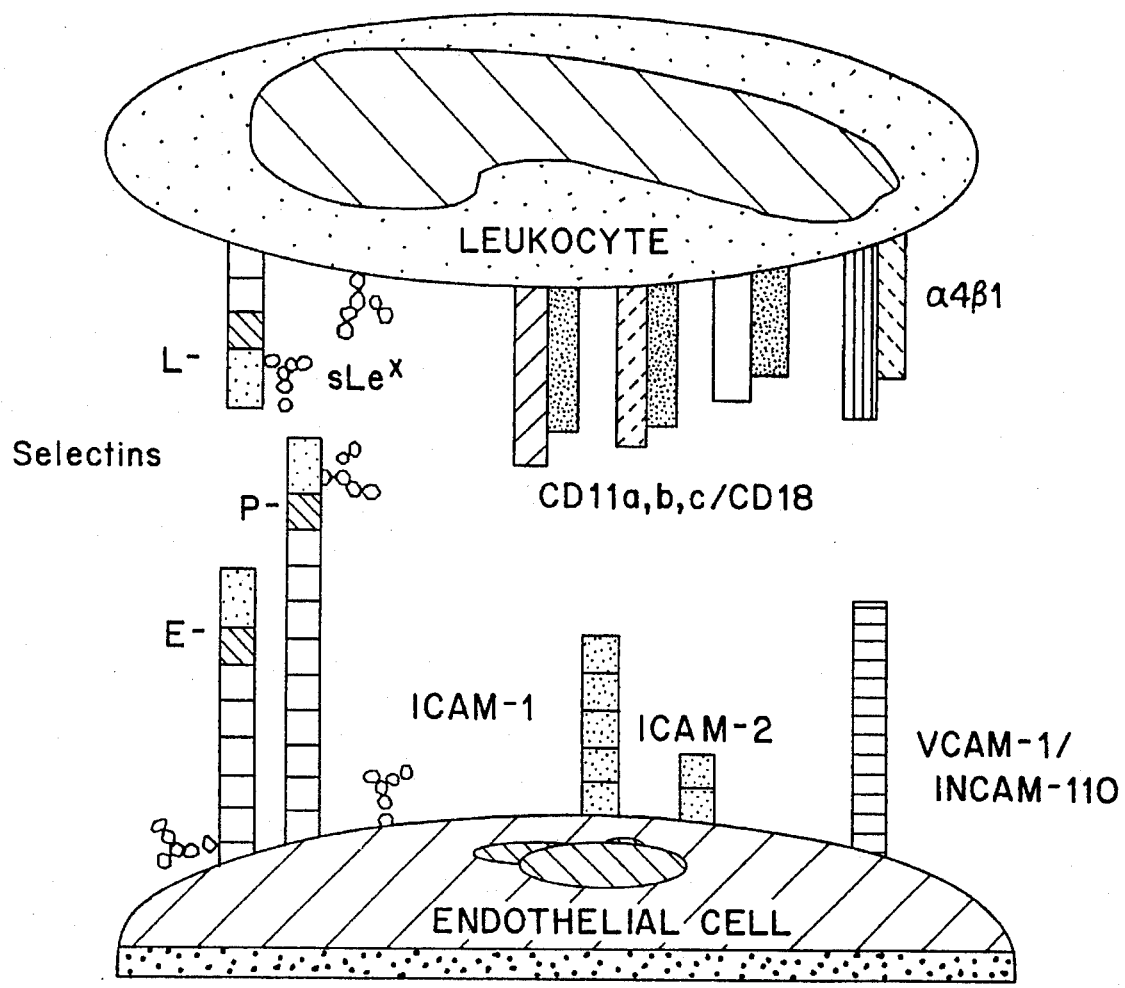
FIG. 1 shows a schematic drawing of the molecules involved in leukocyte adhesion to the vessel wall.
Figure 2:
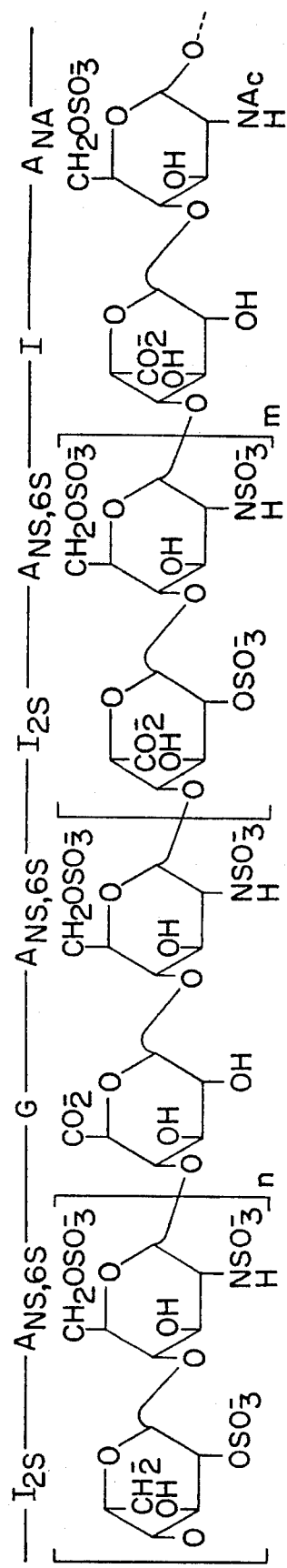
FIG. 2 shows the structure of representative saccharide sequences found in heparin.

The present invention provides a method of modulating selectin receptor binding in a subject comprising administering to the subject an effective amount of an oligosaccharide which binds to the selectin receptor, wherein the oligosaccharide has the structure of a heparin or heparin-like molecule containing from about 2 to about 50 saccharide units as long as oligosaccharides from about 18 to about 50 units in length are antithrombin (AT-III) binding-pentasaccharide free (i.e., do not contain the specific AT-III binding pentasaccharide). Preferably, the oligosaccharide is used in ameliorating P- and L-selectin receptor binding associated disorders such as inflammatory processes, specific immunological disease processes, infection with viruses or bacteria, malignancy and metastasis, and reperfusion injury, for example.

The term "modulate" refers to controlling the binding of a natural ligand to the selectin receptor by blocking the receptor with an oligosaccharide which binds the receptor. The oligosaccharide is useful for ameliorating a disorder associated with selectin receptor binding in a subject. The term "ameliorate" denotes a lessening of the detrimental effect of the selectin receptor binding associated disease in the subject receiving therapy. The method of the invention is useful for ameliorating the disease by administering an oligosaccharide which has the structure of heparin or heparin-like molecules is from about 2 to about 50 saccharide units to inhibit binding of a natural ligand to a selectin receptor, with the caveat that oligosaccharides from 18 to 50 units in length are AT-III-binding-pentasaccharide free. Preferably, the selectin-receptor in the method of the invention is the P- or L-selectin receptor.

As used herein in the chemical formulae for carbohydrates "ΔUA" means uronic acid with an unsaturation between carbons 4 and 4 (4,5 unsaturated uronic acid); "ΔUA2S" means 2 O-sulfated, 4,5 unsaturated uronic acid;

"GlcN" means D-glucosamine; "GlcN6S" means 6 O-sulfated D-glucosamine; "IdoA" means L-iduronic acid; "IdoA2S" means 2 O-sulfated L-iduronic acid; and "GlcA" means D-glucuronic acid.

An effective amount of the oligosaccharide is administered to the subject according to the method of the invention. The term "effective amount" refers to that amount of oligosaccharide which is administered in sufficient quantity to bind to the selectin receptor to block the natural ligand from binding, thereby ameliorating any selectin receptor binding associated disorder.

Since leukocyte adhesion to the vascular wall is a key, early step in inflammation, therapies directed at preventing this step are attractive for the treatment of pathologic inflammation. E- and P- selectin expression is induced in endothelial cells (and platelets in the case of P-selectin) rather than constitutive and therefore is concentrated in areas of inflammation. L-selectin is constitutively expressed in leukocytes and shed upon cell activation. This means that adhesion inhibitors would only be required locally and, consequently, would be effective at lower doses than inhibitors aimed at constitutively expressed molecules. Such therapies may be cheaper and less toxic than currently available therapies.

Preferably the oligosaccharide used in the method of the invention is from about 2 to about 17 saccharide units. However, oligosaccharides from about 18 to about 50 saccharides are included as long as they do not contain the ATIII-specific binding pentasaccharide. Most preferably, the oligosaccharide has the structure of heparin or a heparin-like molecule and is four to six saccharides. The oligosaccharide used in the method of the invention is a small heparin-like fragment which includes fragments modified, for example, by the addition or removal of functional groups, as long as the fragment is still capable of binding to and blocking selectin receptors. Such modifications include addition or removal of sulfate groups, addition of phosphate groups and addition of hydrophobic groups such as aliphatic or aromatic aglycones. Modifications also include the addition of non-heparin saccharide residues such as sialic acid, galactose, fucose, glucose, and xylose. A preferable oligosaccharide useful in the method of the invention has the structure ΔUA2Sα1–4 DGlcNS6Sα1–4LIdoA2Sα1–4DGlcNS6S (F4) or modifications thereof. Hexa- and octasaccharides that are extensions of the F4 tetrasaccharide above, by one and two disaccharide units which are included in the invention, include ΔUA2Sα1–4DGlcNS6Sα1–4LIdoA2Sα1–4DGlcN6Sα1–4LIdoA2Sα1–4DGlcN6S and ΔUA2Sα1–4DGlcNs6Sα1–4LIdoA2Sα1–4DGlcN6Sα1–4LIdoA2Sα1–4DGlcN6Sα1–4LIdoA2α1–4DGlcN6S. F4 hexasulfated tetrasaccharides are preferred, however, pentasulfated heparin tetrasaccharides such as ΔUA2Sα1–4DGlcNS6Sα1–4LIdoA2Sα1–4DGlcN6S and ΔUA2Sα1–4DGlcNS6Sβ1–4DGlcAα1–4DGlcNS6S are useful in the method of the invention.

The oligosaccharides useful in the method of the invention may be a fragment of naturally occurring heparin or heparin-like molecule such as heparan sulfate or other glycosaminoglycans, or may be synthetic fragments. The synthetic fragments could be modified in saccharide linkage in order to produce more effective blockers of selectin binding. Methods for producing such saccharides will be known by those of skill in the art (see for example: M. Petitou, Chemical Synthesis of Heparin, in Heparin, Chemical and Biological Properties, Clinical Applications, 1989, CRC Press Boca Raton, Fla., D. A. Lane and V. Lindahl, eds. pp. 65–79).

The oligosaccharides useful in the method of the invention may be a mixture of molecules containing from about 2 to about 50 saccharide units or may be homogeneous fragments as long as the number of saccharide units is 2 or more, but not greater than about 50. Oligosaccharides from about 18 to about 50 saccharide units are ATIII-binding-pentasaccharide free. In addition, the saccharide units may be multimerized, so long as the total number of saccharide units does not allow bridge formation between thrombin and antithrombin. For example, two tetrasaccharides or two hexasaccharides may be joined by a spacer moiety and used to bind a selectin receptor. Those of skill in the art can produce various multimeric combinations of the appropriate saccharide units without resort to undue experimentation.

The oligosaccharide may be administered to a patient according to the method of the invention to ameliorate P- and L-selectin receptor binding associated disorders, for example. One such disorder in which the oligosaccharide may be administered to a patient is for the treatment of inflammation. The oligosaccharides used in the method of the invention can be administered parenterally by injection or by gradual perfusion over time. The oligosaccharides can also be administered intravenously, intraperitoneally, intramuscularly, subcutaneously, intracavity, or transdermally. Oligosaccharides may also be administered orally or by inhalation. For example, when used therapeutically for treatment of an inflammatory disorder of the lungs, a preferred route of administration would be by a pulmonary aerosol. By blocking the P- and L-selectin receptors, leukocyte adhesion to endothelium at the site of inflammation is blocked.

Administration of the oligosaccharide in the method of the invention may also be used for ameliorating post-reperfusion injury. When treating arterial thrombosis, induction of reperfusion by clot lysing agents such as tissue plasminogen activator (t-PA) is often associated with tissue damage. Such tissue damage is thought to be mediated at least in part by leukocytes including but not limited to polymorphonuclear leukocytes (PMN). Therefore administration of the oligosaccharide would block leukocyte or PMN-endothelial interactions, and thereby diminish or prevent post-reperfusion injury.

The method of the invention can also be used to prevent adhesion of leukocyte tumor cells or non-leukocyte tumor cells to endothelial tissue. Thus, administration of a 4 to 6 saccharide which binds to a selectin, such as P- or L- for example, would prevent metastatic spread of tumor cells.

The method of the invention is also useful for the treatment of microbial infections. Many microbes, such as bacteria, rickettsia, various parasites, and viruses, bind to vascular endothelium and leukocytes, and in some cases, possibly to P- and L-selectin. Thus, the oligosaccharides used in the method of the invention may be administered to a patient to prevent binding of a microbe which uses a selectin receptor as its binding target molecule, thereby modulating the course of the microbial infection.

The method of the invention can be used to treat vasculitis by administering to a patient the oligosaccharide described above. Tissue damage associated with focal adhesion of leukocytes to the endothelial lining of blood vessels is inhibited by blocking the P- and L-selectin receptors.

The dosage ranges for the administration of the oligosaccharides in the method of the invention are those large enough to produce the desired effect in which the symptoms of the P- and L-selectin receptor associated disease are ameliorated. The dosage should not be so large as to cause adverse side effects. Generally, the dosage will vary with the age, condition, sex and extent of the disease in the patient and can be determined by one of skill in the art. The dosage can be adjusted by the individual physician in the event of any complication. When used for the treatment of inflammation, post-reperfusion injury, leukemia, lymphoma, microbial/viral infection, vasculitis, or inhibition of the metastatic spread of tumor cells, for example, the oligosaccharide may be administered at a dosage which can vary from about 1 mg/kg to about 1000 mg/kg, preferably about 1 mg/kg to about 50 mg/kg, in one or more dose administrations daily, for one or several days. For certain long term disease processes (e.g., rheumatoid arthritis) the oligosaccharide may be administered regularly or intermittently for a period of weeks to months or years.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

Controlled delivery may be achieved by selecting appropriate macromolecules, for example, polyesters, polyamino acids, polyvinyl pyrrolidone, ethylenevinylacetate, methylcellulose, carboxymethylcellulose, protamine sulfate, or lactide/glycolide copolymers. The rate of release of the oligosaccharide may be controlled by altering the concentration of the macromolecule.

Another method for controlling the duration of action comprises incorporating the oligosaccharides into particles of a polymeric substance such as polyesters, polyamino acids, hydrogels, polylactide/glycolide copolymers, or ethylenevinylacetate copolymers. Alternatively, it is possible to entrap the oligosaccharides in microcapsules prepared, for example, by coacervation techniques or by interfacial polymerization, for example, by the use of hydroxymethylcellulose or gelatin-microcapsules or poly(methylmethacrolate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The following examples are intended to illustrate but not limit the invention. While they are typical of those that might be used, other procedures known to those skilled in the art may alternatively be used.

EXAMPLE 1

IN VITRO ADHESION ASSAYS

Heparin tetrasaccharide and heparin hexasaccharide fragments (size-fractionated mixtures) were obtained from Enzyme Research Laboratories, South Bend, Ind. Crude heparin and dermatan sulfate were obtained from Sigma Chemical Company, St. Louis, Mo. LMW heparin oligosaccharide (Enzyme Research Laboratories, South Bend, Ind.) was prepared by size fractionation of crude porcine heparin.

Heparin oligosaccharides (Enzyme Research Laboratories) were prepared by chemical cleavage of crude porcine heparin (benzyl-esterification of carboxyl groups of iduronic acid followed by base-induced β-elimination) and multi-step fractionation using ethanol precipitation and high performance liquid chromatography (HPLC). Crude heparin from porcine intestinal mucosa (Cat. #H3393), de-N-sulfated heparin (Cat. #D4776), tris-sulfated heparin disaccharide (▲UA2Sα1–4GlcNS6S), and heparan sulfate (Cat. #H7641) were from Sigma Chemical Company, St. Louis, Mo. The heparin tetrasaccharide F4 was size-fractionated from enzymatically depolymerized porcine heparin using strong anion exchange HPLC, as previously described (R. J. Linhardt, et al., $Biochem. J.$, 254:781, 1988; K. G. Rice, et al., $Biochem. J.$, 244:515, 1987; Z. M. Merchant, et al., $Biochem. J.$ 229:369, 1985; identity and purity were established using two-dimensional 500-MHz $^1$H NMR, fast atom bombardment-mass spectroscopy, and gradient polyacrylamide gel electrophoresis (Z. M. Merchant, et al., $Biochem. J.$ 229:369, 1985; L. M. Mallis, et al., $Anal. Chem.$ 61:1453, 1989).

COS cells were grown on coverslips in Dulbecco's minimal essential media with 10% fetal calf serum. After 72 hours, polysaccharides were added to the COS cell cultures to achieve final concentrations of 0, 0.1, 1.0, 10.0, 100.0 or 1000.0 µg/ml. Polysaccharides included crude heparin, dermatan sulfate, heparin tetrasaccharide, and heparin hexasaccharide. HL60 cells, a leukocytic cell line, were added to the COS cell cultures 30 minutes after the polysaccharides were added and incubated for 30 minutes. The coverslips were then washed with media to remove unbound cells and COS cells with three or more HL60 cells bound (rosettes) were counted using phase contrast microscopy.

cDNAs encoding full length transmembrane forms of E-, P-, or L-selectin (in pCDM7 or pCDM8; Aruffo, A., Kolanus, W., Walz, G., Fredman, P., and Seed, $Cell$, 67:35–44, 1991) were transfected into COS cells using DEAE-dextran. Briefly, subconfluent monolayers were incubated at 37° C. for 2.5 hours with Dulbecco's modified Eagle's medium (DMEM) with 10% NuSerum (Collaborative Research, Bedford, Mass.) containing 10 µg cDNA, 400 µg/mL DEAE-dextran (Sigma), and 100 µM chloroquine diphosphate (Sigma). After removal of the transfection mixture, monolayers were incubated at room temperature for 2 minutes with 10% dimethylsulfoxide (Sigma) in DPBS and then allowed to grow in regular medium (DMEM-10% FCS) for 12–18 hours. These cells were transferred to 24-well plates (Costar, Cambridge, Mass.) containing gelatin-coated coverslips, and cultured for an additional 24–48 hours. HL60 cells were applied and incubated at 4° C. or 37° C. for 30 minutes. Non-adherent cells were removed by immersing the coverslips in DPBS and the adherent cells were fixed with 2.5% glutaraldehyde in DPBS and counted microscopically. HL60 cells were fixed with 2.5% glutaraldehyde in DPBS and counted microscopically. HL60 cell adhesion was quantitated as number of HL60 rosettes (2 or more cells bound) per 100 transfected COS cells. Number of transfected COS was determined using mAbs specific for E-, P-, and L-selectin (see below) followed by secondary reaction with a fluorescein-conjugated anti-immunoglobulin antibody (Cappel, Durham, N.C.).

Figure 3:
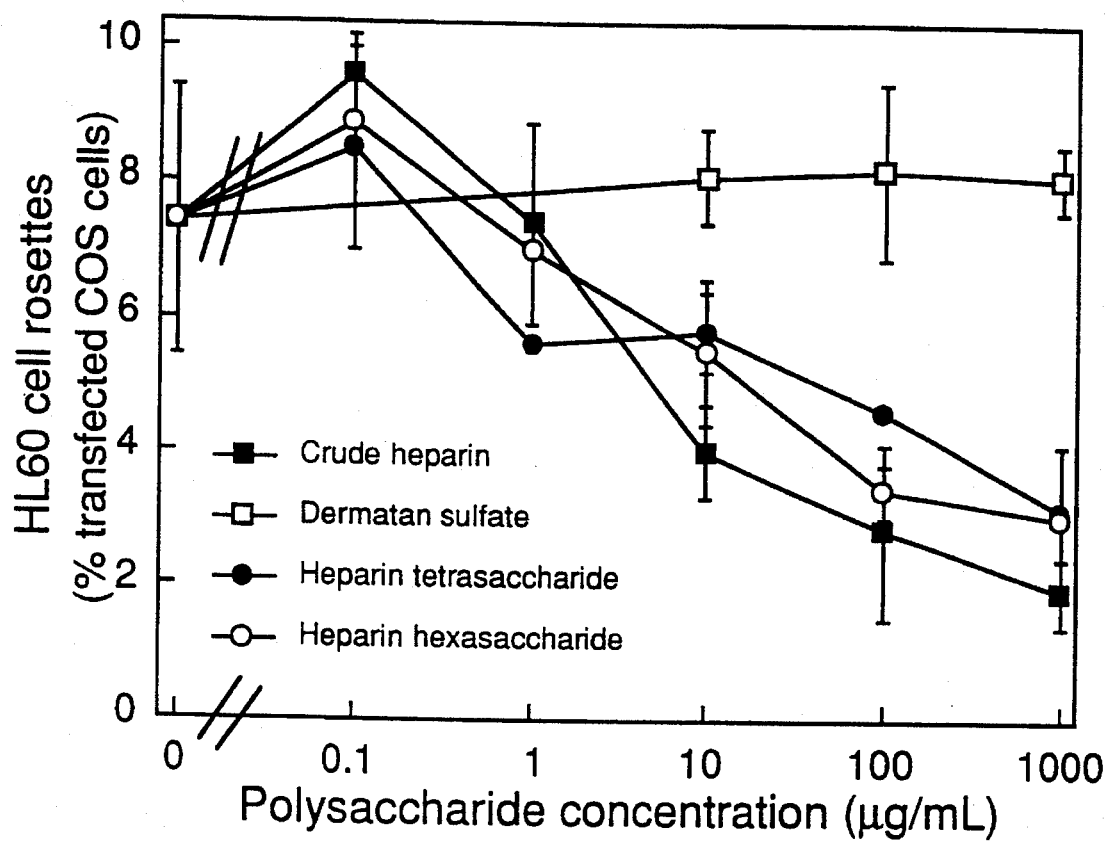
FIG. 3 shows inhibition by heparins of HL60 cell adhesion to COS cells transfected with P-selectin cDNA.
Figure 4A:
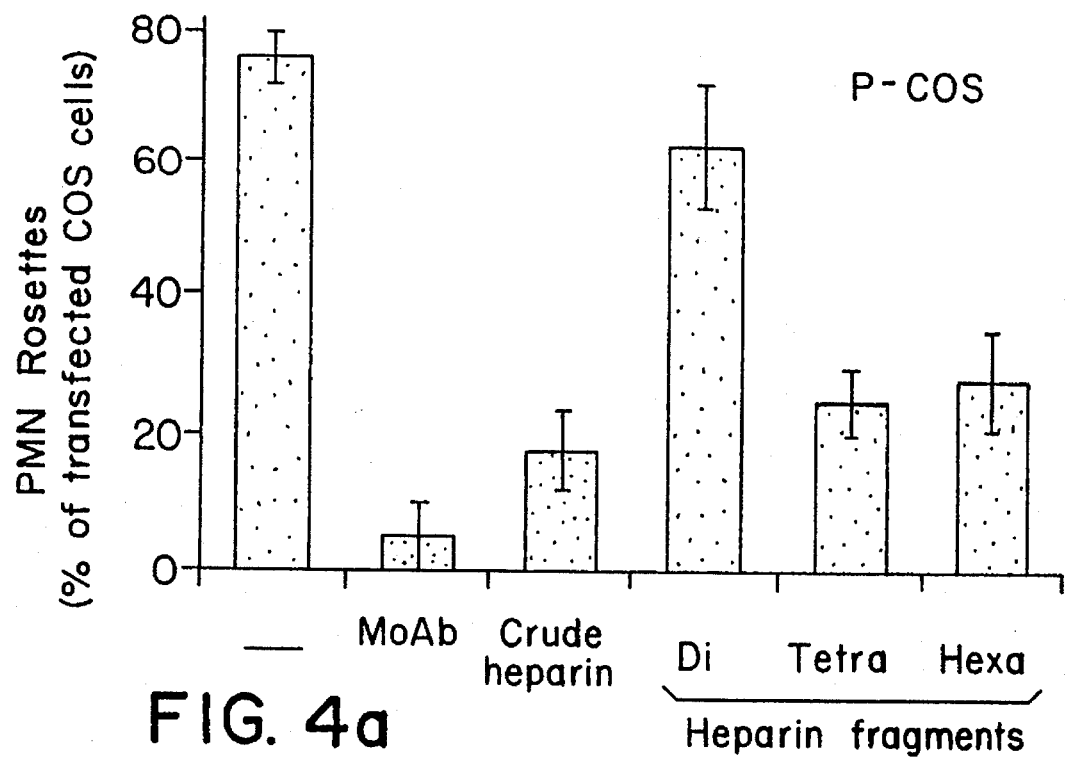
FIG. 4 shows the effect of heparins on PMN adhesion to P- and E-COS cells.
Figure 4B:
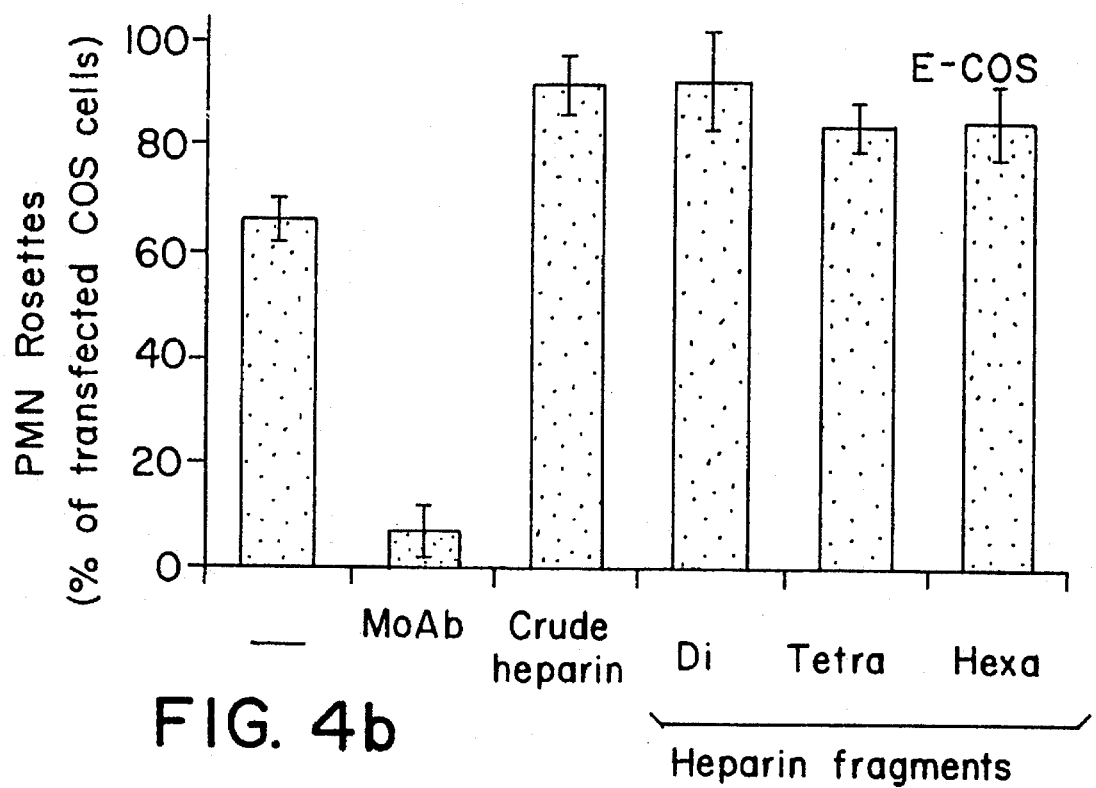

FIG. 3 shows the results of cell adhesion of HL60 cells to COS cells after the COS cells were transfected by DEAE Dextran method (Seed, B., and Aruffo, A., $Proc. Natl. Acad. Sci., USA$ 84:3365–3369, 1987; Aruffo, A., in Current Protocols in Molecular Biology Vol. 2, pp. 16.13.1–16.13.7, Greene Publishing Associates and Wiley-lnterscience, 1991, New York, N.Y.) with cDNA encoding full length P-selectin Johnston, et al., *Cell* 56:1033–1044, 1989. L-selectin (Siegelman, M. H., et al., *Science,* 243:1165–1172, 1989; Lasky, L. A., et al., *Cell,* 56:1045–1055, 1989) or E-selectin (Bevilacqua, M. P., et al., *Science,* 243:1160–1165, 1989). Tetrasaccharide and hexasaccharide fragments of heparin blocked the adhesion of HL60 cells to COS cells transfected with cDNAs encoding P- or L-selectin, but not E-selectin. In addition, these heparin fragments blocked the adhesion of human polymorphonuclear leukocytes (PMNs, neutrophils) to P-COS, but not to E-COS (FIG. 4). Human PMNs were isolated from freshly drawn heparinzed blood by centrifugation through a double-density gradient of Histopauque 1077 and 1119 (Sigma), essentially as described (English, D., and Anderson, B. R., *J. Immunol. Methods,* 5:249–254, 1974). Isolated PMN were incubated with COS cells transfected with P- or E-selectin cDNAs. Carbohydrates or antibodies were added to the COS cells 30 minutes prior to addition of PMNs to achieve a final concentration of 1 mg/ml. The blocking monoclonal antibodies were G1 (P-selectin) (R. McEver, University of Oklahoma) and H18/7 (E-selectin) (University of California, San Diego). A trisulfated disaccharide fragment of heparin ($\alpha\Delta$UA-2S[1–4] GlcNS-6S) had little blocking activity at the concentrations tested in these adhesion assays, but was somewhat effective in the competition ELISA on L-selectin (see below).

Figure 5A:
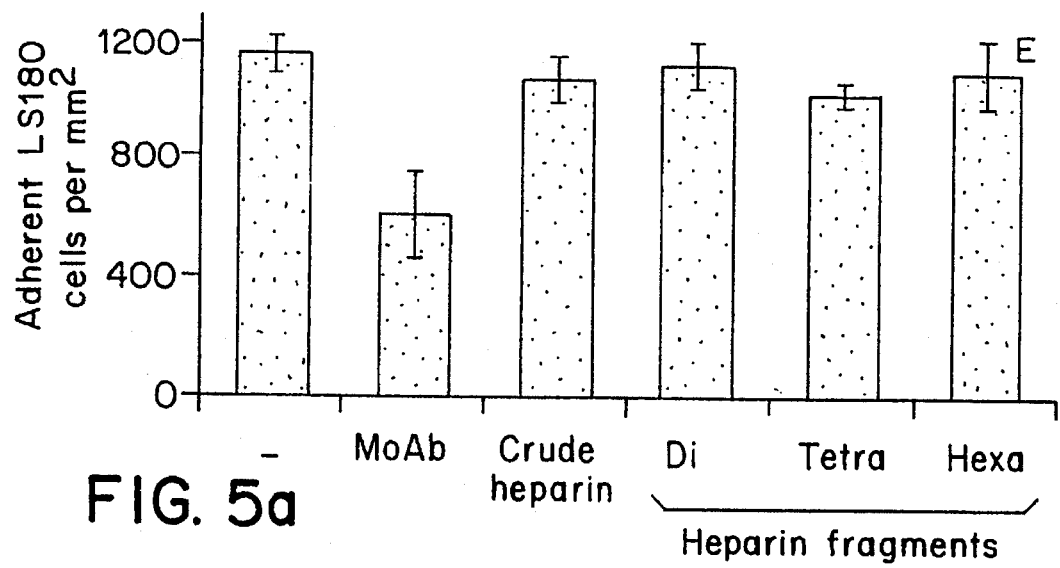
FIG. 5 shows the effect of heparins on the adhesion of LS180 colon cancer cells to immobilized selectin-Ig fusion proteins.
Figure 5B:
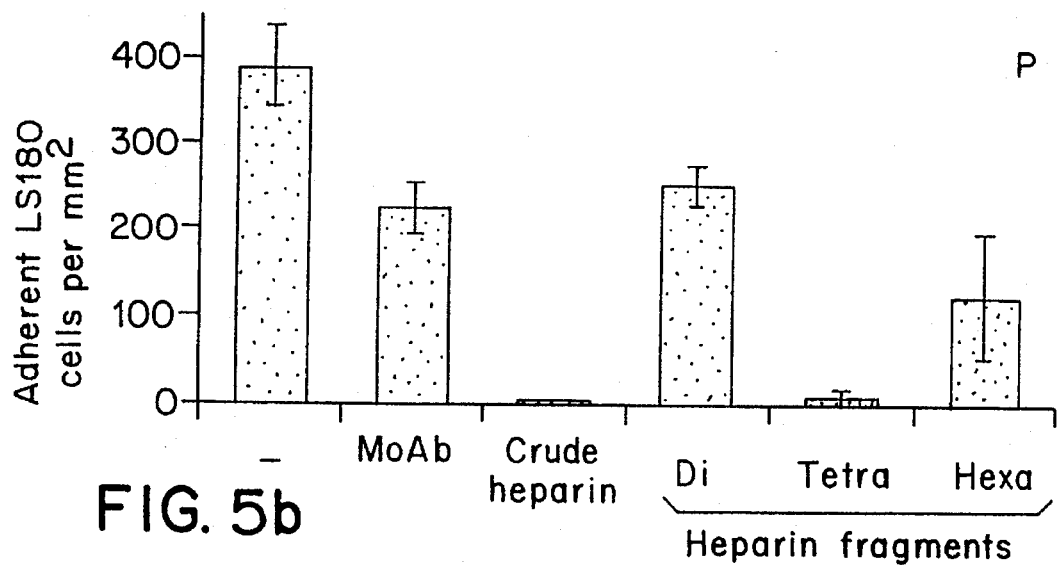
Figure 5C:
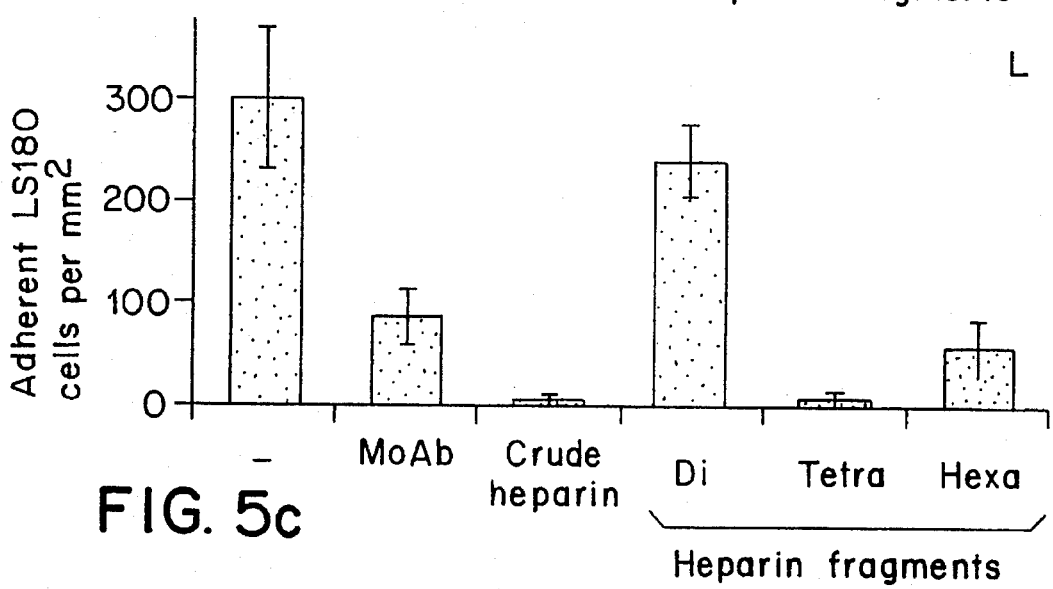

The colon carcinoma cell line, LS180, is a useful model for studying selectin-dependent adhesion since it binds to all three selectins. E-, P-, and L-selectin-Ig were immobilized on microwell (Terasaki) plates coated with protein A. Five µl of buffer containing crude heparin, di-, tetra- or hexasaccharide heparin fragments or antibody (as described above) was incubated for 20 minutes at 4° C. Five µl containing 5000 LS180 cells was added for 30 minutes at 4° C. to allow adhesion to occur. The wells were then washed, fixed with glutaraldehyde, and the bound cells counted by microscopic observation. FIG. 5 shows that hexasaccharide and tetrasaccharide fragments of heparin inhibited the adhesion of LS180 cells to plates coated with P- and L-selectin-Ig, but not E-selectin-Ig. The heparin disaccharide had no effect at the same concentration based on weight (a two-fold higher molar concentration compared to the tetrasaccharide).

Figure 6:
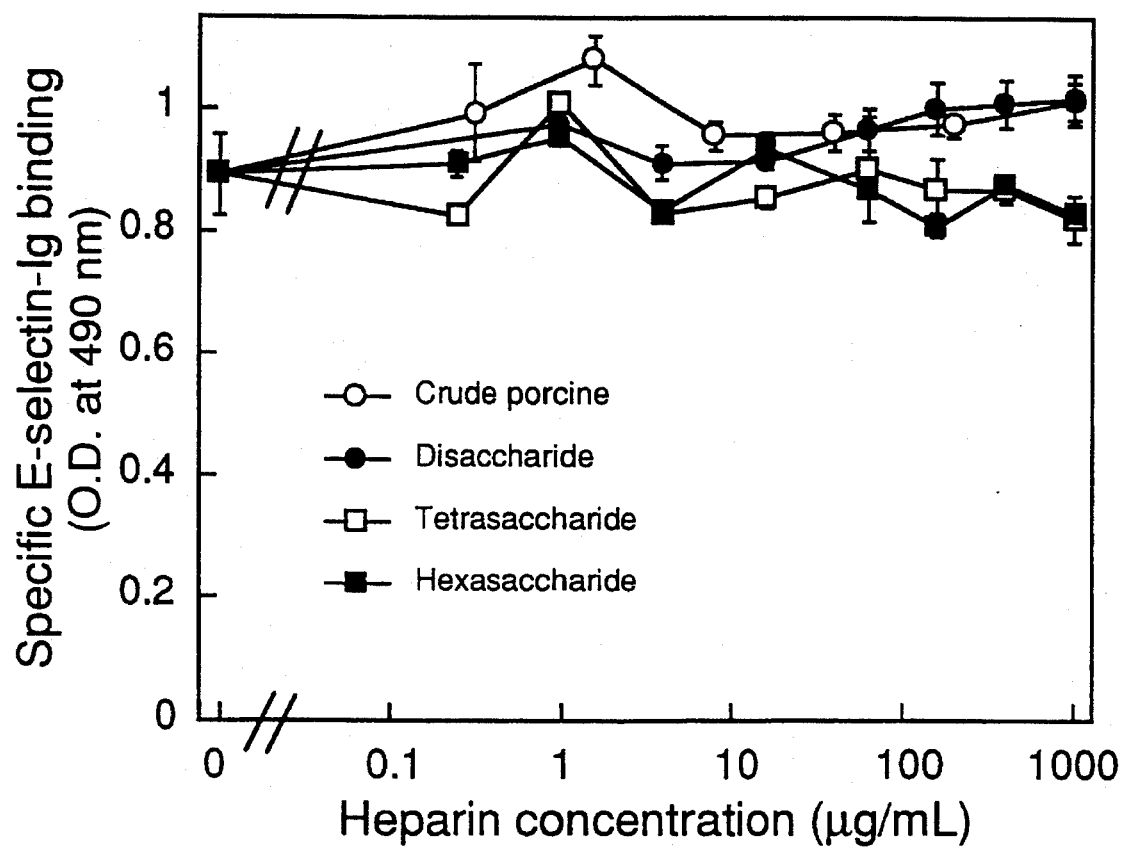
FIG. 6 shows heparin inhibition curves of E-selectin-Ig binding to immobilized BSA-sLe$^x$.
Figure 7:
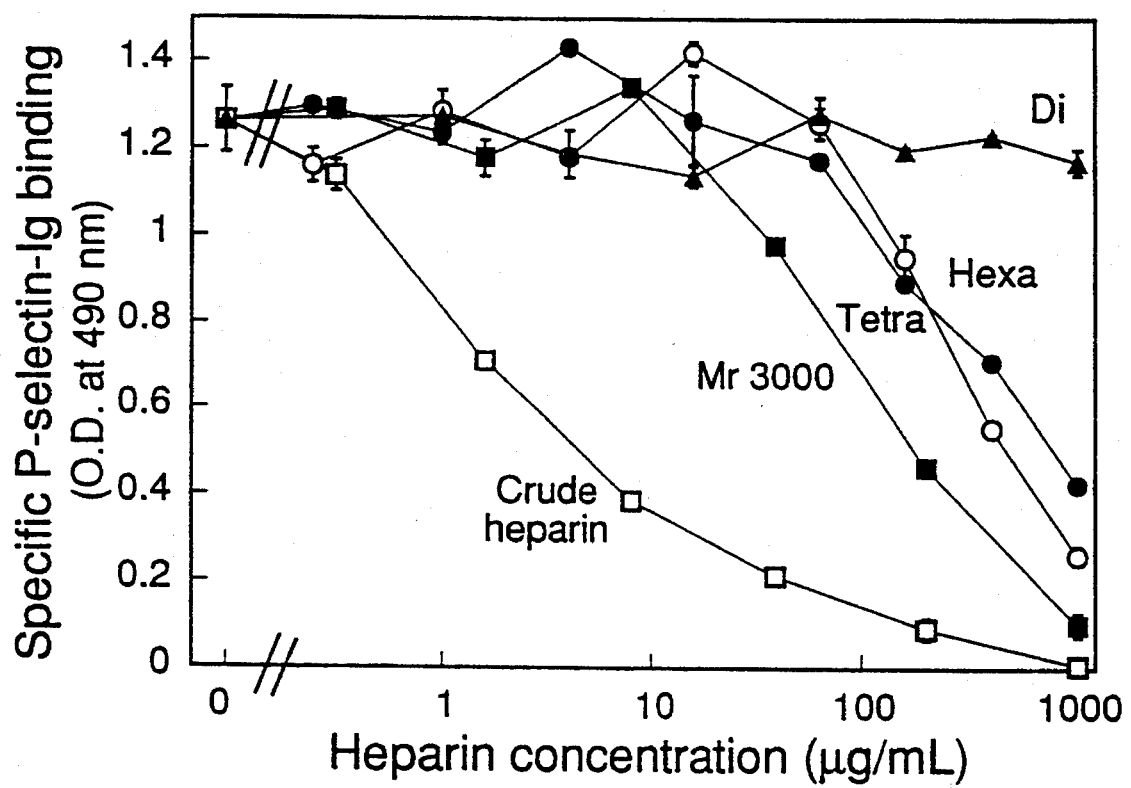
FIG. 7 shows heparin inhibition curves of P-selectin-Ig binding to BSA-sLe$^x$.
Figure 8:
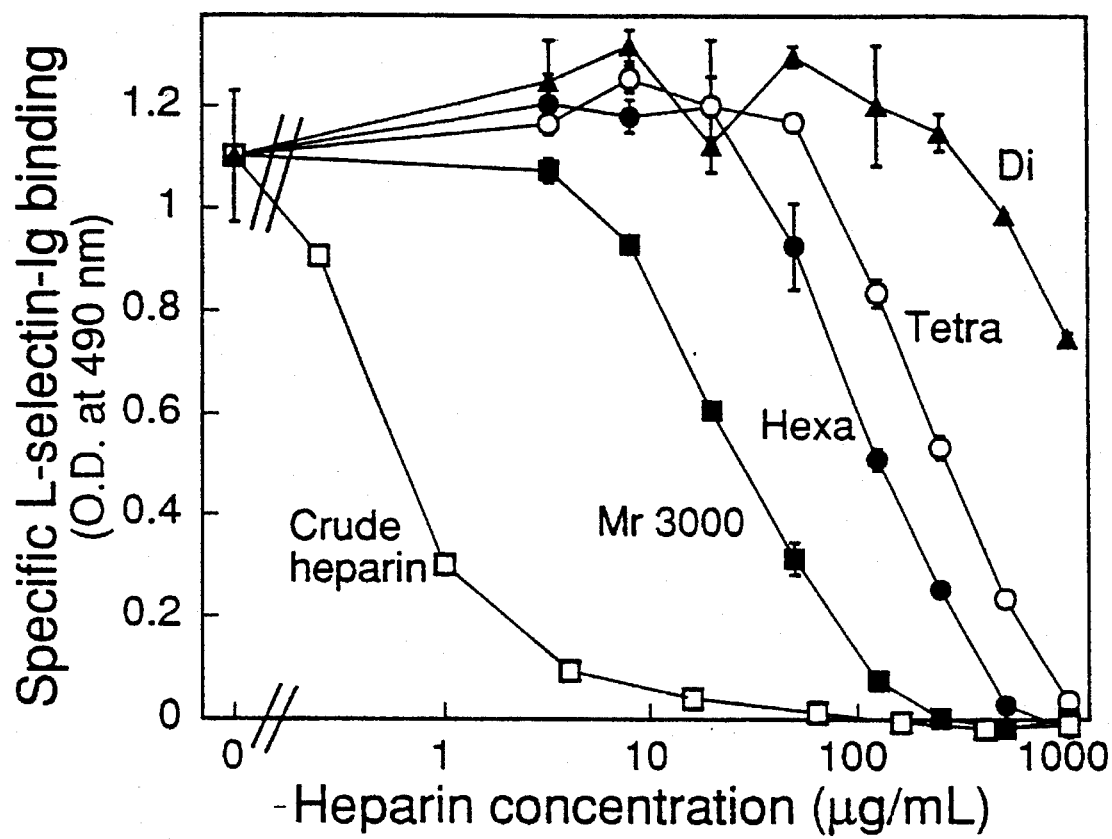
FIG. 8 shows heparin inhibition curves of L-selectin-Ig binding to BSA-sLe$^x$.

The effects of heparin fragments on the direct binding interaction of selectins with carbohydrate ligands were studied using a competitive ELISA, essentially as described by Nelson, R. M., et al. (*J. Clin. Invest.* 91:1157–1166, 1993). Briefly, microtiter plates were coated with neoglycoprotein BSA-sLe$^x$, BSA-sLe$^a$, (Chembiomed, Alberta, CAN) or unconjugated BSA (0.11 µg/well) in 50 mM carbonate bicarbonate buffer, pH 9.5. Plates were blocked with 20 mg/ml BSA in ELISA buffer (150 mM NaCl, 20 mM HEPES, 2 mM CaCl$_2$, 0.25 mM thimerosal, pH 7.4). E- and P-selectin-Ig fusion proteins (20 nM) were coincubated in the coated, blocked microtiter wells with serially diluted heparin fragments (typically 0–1000 µg/ml) in ELISA buffer containing 10 mg/ml BSA for three hours at room temperature. Wells were washed with ELISA buffer, and bound selectin-Ig detected by incubation for 30 minutes with peroxidase-conjugated goat anti-human IgG(Fc) antibody (1:6,000 in ELISA buffer containing 10 mg/ml BSA) followed by washing and addition of o-ophenlyene-diamine-dihydrochloride substrate (OPD, 0.8 mg/ml in 50 mM sodium phosphate, 50 mM sodium citrate buffer, pH 5.0, 0.015% hydrogen peroxide, 200 µl/well) and optical density (450 nm) measured at 12–20 second intervals. Color development was stopped in the linear range (typically after 4–16 minutes) using 5 µl 4 NH$_2$SO$_4$, and endpoint optical density measured at 490 nm. For L-selectin-Ig binding, the assay was performed as described previously (Foxall, C., et al., *J. Cell Biol.,* 117:895–902, 1992), except L-selectin-Ig aggregation was accomplished using perioxidase-conjugated goat anti-Human IgG(Fc) antibody (1:6000) and 20 nM L-selectin-Ig in ELISA buffer containing 10 mg/ml BSA. Microtiter plates were coated with the neoglycoprotein BSA-sLe$^x$ or BSA-sLe$^a$ (Chembiomed, Ltd. Alberton, Canada) made as described by Lemieux, R. V., et al. (*J. Am. Chem. Soc.,* 97:4076–4083, 1975) and Pinto, B. M., et al. (*Carbohydrate Res.,* 124:313–318, 1983), to support the binding of E-, P-, and L-selectin-Ig fusion proteins (20–50 nM) (Walz, G. A., et al., *Science,* 250:1132–1135, 1990; Aruffo, A., et al., *Cell,* 67:35–44, 1991; Aruffo, A., et al., *Proc. Natl. Acad. Sci.* 89:2292, 1992). FIGS. 6, 7, and 8 show the mean and range of duplicate wells, except at 0 µg/ml heparin, where the values are the mean and standard deviation of 6 wells.

Figure 9:
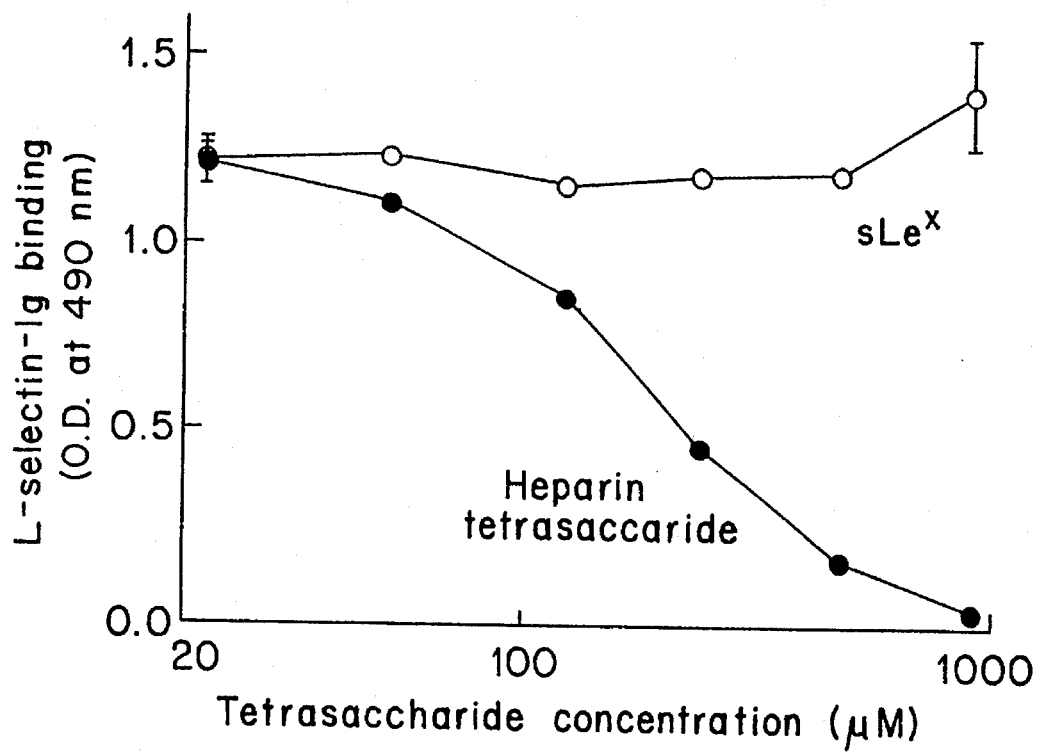
FIG. 9 shows a comparison of heparin tetrasaccharide and sLe$^x$ tetrasaccharide inhibition of L-selectin-Ig binding to BSA-sLe$^a$.
Figure 10:
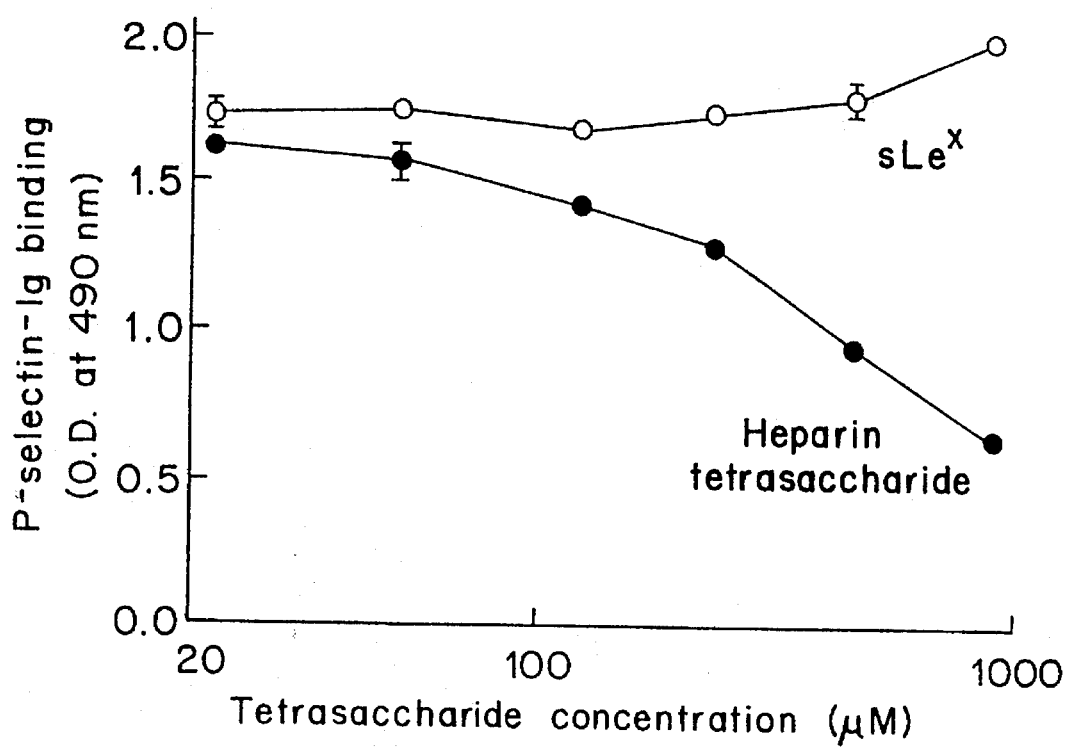
FIG. 10 shows a comparison of heparin tetrasaccharide and sLe$^x$ tetrasaccharide inhibition of P-selectin Ig binding to BSA-sLe$^x$.

The ability of solution-phase carbohydrates related to sLe$^x$ and sLe$^a$ has previously been quantitated (Nelson, et al. supra., 1993). Determination of IC$_{50}$ values (concentration of inhibitor required to reduce binding to 50% of maximum) allows comparison of relative blocking activity. Although heparin fragments had no effect on E-selectin-Ig binding to BSA-sLe$^x$ at concentrations up to 1 mg/ml (FIG. 6), tetrasaccharide and hexasaccharide, fragments of heparin inhibited the binding of P- and L-selectin Ig to plates coated with BSA-sLe $^x$ (FIGS. 7 and 8). A tris-sulfated heparin disaccharide $\Delta$UA2S$\alpha$1–4GlcNS 6S) showed some inhibition of L-selectin-Ig binding (FIG. 8). Comparisons of heparin tetrasaccharides to sLe$^x$ in blocking L- and P-selectin Ig binding to BSA-sLe$^x$ are shown in FIGS. 9 and 10.

Figure 11:
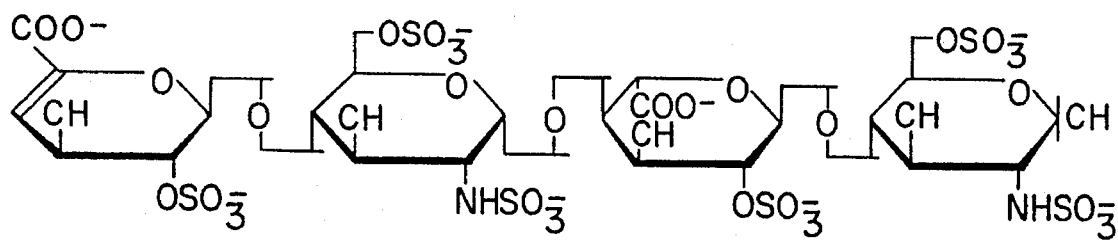
FIG. 11 shows a Haworth projection representation of a hexasulfated heparin tetrasaccharide designated F4.
Figure 12:
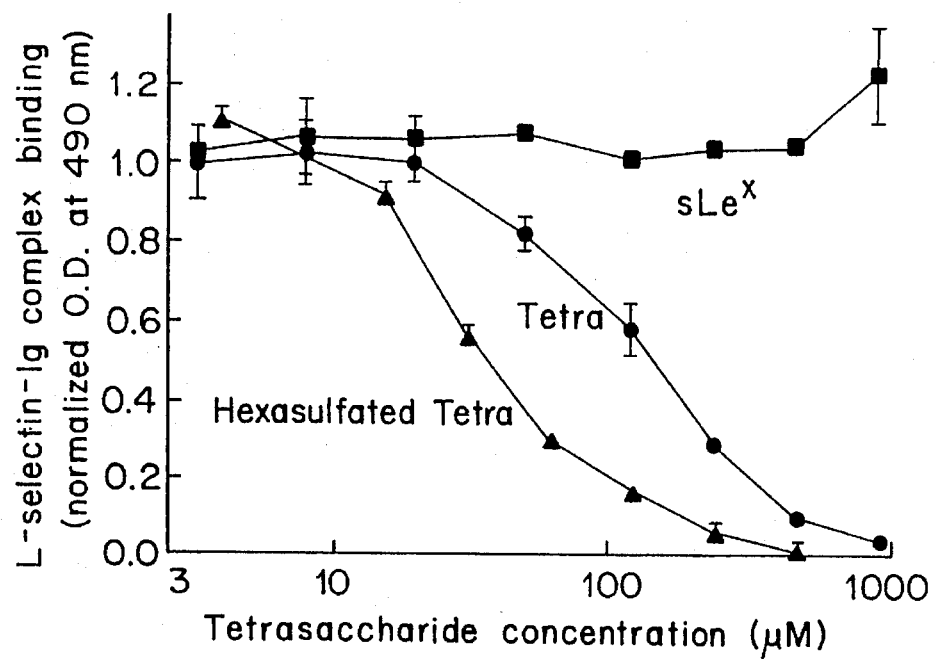
FIG. 12 shows a comparison of the heparin tetrasaccharide F4,▲; size-defined heparin tetrasaccharides, ●; and the sLe$^x$ tetrasaccharide, ■; as inhibitors of L-selectin-Ig binding to BSA-sLe$^x$ in competition ELISA.

A homogenous hexasulfated tetrasaccharide species, F4 (FIG. 11) ($\Delta$UA2S$\alpha$1–4DGlcNS6S$\alpha$1–4LIdoA2S$\alpha$1–4DGlcNS6S) was found to be more active (2–4 fold) than the size fractionated tetrasaccharide mixture, which contains F4 along with other tetrasaccharides having fewer sulfate moieties. In the competition ELISA (as described above), the F4 molecule inhibited L-selectin-Ig with an IC$_{50}$ of 61 µg/ml (46 µM) (FIG. 12), whereas the size-fractionated heparin tetrasaccharides displayed an IC$_{50}$ of 240 µg/ml (20 µM).

By comparison, the sLe$^x$ tetrasaccharide had no measurable activity at concentrations of up to 1 mM in this assay. sLe$^x$ has been reported to block approximately 50% of L-selectin-Ig binding to immobilized sLe$^x$ glycolipid at a concentration of 5 mM (Foxall, et al., *J. Cell. Biol.* 117:895, 1992), and approximately 60% of L-selectin-Ig binding to a high endothelial venule-derived glycoprotein, glycam-1, at 11 mM (Imai, et al., *Glycobiology,* 2:373, 1992). Thus, the F4 heparin tetrasaccharide appears to be over 100-fold more active than sLe$^x$ against L-selectin in non-cellular assays. Consistent with previous studies, sLe$^x$ blocked E-selectin-Ig binding to immobilized BSA-sLe$^x$ with an IC$_{50}$ of 510±60 µM; the F4 heparin tetrasaccharide, like the heparin tetrasaccharide mixture, had no activity against E-selectin-Ig at concentrations up to 1 mM.

Table 1 summarizes the approximate IC$_{50}$ values (µg/ml) of compounds that inhibit selectin-Ig binding to BSA-sLe$^x$.

TABLE 1

| IC$_{50}$ VALUES (µg/ml) OF COMPOUNDS THAT INHIBIT SELECTIN Ig BINDING TO BSA-sLE$^x$ | | |
| --- | --- | --- |
| | L-selectin | P-selectin |
| sLex | 4100[1] | >1000 |

TABLE 1-continued

IC$_{50}$ VALUES (µg/ml) OF COMPOUNDS THAT
INHIBIT SELECTIN Ig BINDING TO BSA-sLE$^x$

|          | L-selectin | P-selectin |
|----------|------------|------------|
| Di       | >1000      | >1000      |
| Tetra Mix| 240        | 1019       |
| Hexa     | 115        | 496        |
| Octa     | 86         | 233        |
| Deca     | 57         | 139        |
| Mr 3000  | 28         | 105        |
| Heparin  | 0.4        | 3          |

[1]Foxall, et al., supra.

EXAMPLE 2

IN VIVO EFFECTS OF HEPARIN FRAGMENTS

The effects of LMW heparin fragments (Mr 3000) on acute inflammation were studied in vivo. Mice were injected with thioglycollate (3% solution) into the peritoneal cavity to induce an inflammatory response. Briefly, mice were given intraperitoneal injections of either saline or 200 µl thioglycollate at time 0. The mice received injections of 200 µl saline or saline containing heparin molecules intravenously. Heparin tetrasaccharides and LMW heparin were studied (FIG. 13—LMW heparin, 1 mg/mouse; tetra, 1 mg/mouse). At two hours the mice were sacrificed and their peritoneal cavities lavaged to collect leukocytes using 10 ml PBS containing 10 U/ml heparin to prevent clotting.

Following hypotonic lysis of contaminating red blood cells, lavage fluid was examined microscopically for total cells and PMNs. Peritoneal cells were counted in a hemocytometer (2 separate counts per sample). Occasional samples contained small amounts of contaminating red blood cells which were lysed prior to counting. The percentage of neutrophils was assessed by counting cytospin preparations stained with Dif-Quik stain (Baxter, McGaw Park, Ill.: two counts per slide, 300 cells per count). Data are expressed as the mean+S.E.M. of three separate experiments. Experimental groups contained 5–7 animals per experiment; control (i.p. saline) groups contained 1–3 animals per experiment and were consistent with numerous historical controls.

Blocking by LMW heparin and heparin tetrasaccharide was statistically significant at $P<0.001$ in a Student's t-test.

Figure 13:
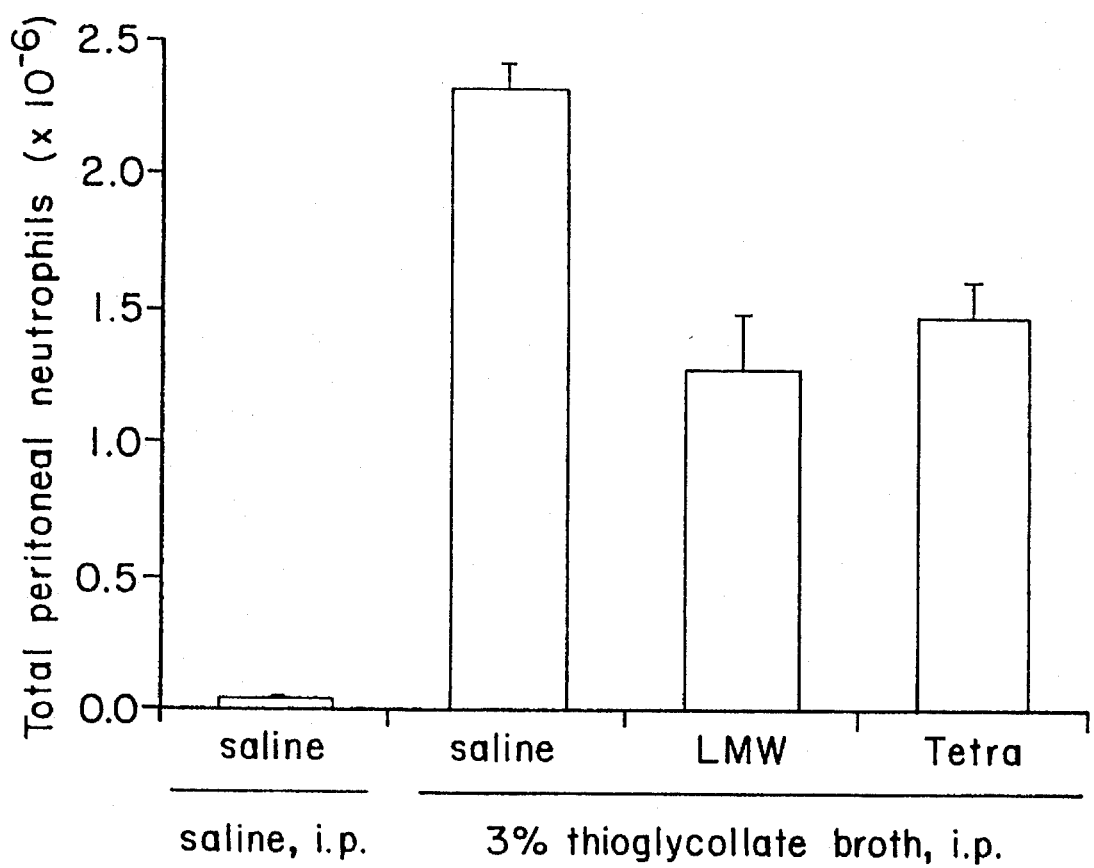
FIG. 13 shows the effect of low molecular weight (LMW) heparin and heparin-derived tetrasaccharides on acute inflammation in vivo.

The inflammatory response was characterized by the influx of PMNs, as shown in FIG. 13. Intravenous injection of the small heparin molecules, including the heparin tetrasaccharides and the LMW fraction inhibited PMN influx into the peritoneal cavity. These heparin treatments did not significantly alter the number of neutrophils in the peripheral blood.

The foregoing is meant to illustrate, but not to limit, the scope of the invention. Indeed, those of ordinary skill in the art can readily envision and produce further embodiments, based on the teachings herein, without undue experimentation.

We claim:

1. A method of modulating selectin receptor binding in a subject comprising administering to the subject an effective amount of an unbranched oligosaccharide which comprises 4 to 8 saccharide units containing 1→4 linked residues of L iduronic or D glucuronic acid alternating with D-glucosamine, and which oligosaccharide binds to a selectin receptor associated with inflammation but lacks a binding site for antithrombin.

2. The method of claim 1, wherein the oligosaccharide is a tetrasaccharide.

3. The method of claim 2, wherein the tetrasaccharide has the structure ΔUA2Sα1–4DGlcNS6Sα1–4L—IdoA2Sα1–4DGlcNS6S.

4. The method of claim 1, wherein the oligosaccharide has the structure ΔUA2Sα1–4DGlcNS6Sα1–4LIdoA2Sα1–4DGlcN6Sα1–4 LIdoA2Sα1–4DGlcN6S.

5. The method of claim 1, wherein the oligosaccharide has the structure ΔUA2Sα1–4DGlcNS6Sα1–4LIdoA2Sα1–4DGlcN6Sα1–4 LIdoA2Sα1–4DGlcN6Sα1–4LIdoA2α1–4DGlcN6S.

6. The method of claim 2, wherein the tetrasaccharide has the structure ΔUA2Sα1–4DGlcNS6Sα1–4LIdoA2Sα1–4DGlcN6S.

7. The method of claim 2, wherein the tetrasaccharide has the structure ΔUA2Sα1–4DGlcNS6Sβ1–4DGlcAα1–4 DGlcNS6S.

* * * * *